United States Patent
Old et al.

(10) Patent No.: US 8,063,033 B2
(45) Date of Patent: Nov. 22, 2011

(54) THERAPEUTIC BETA-LACTAMS

(75) Inventors: David W. Old, Irvine, CA (US); Danny T. Dinh, Garden Grove, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 404 days.

(21) Appl. No.: 12/352,903

(22) Filed: Jan. 13, 2009

(65) Prior Publication Data

US 2009/0186866 A1    Jul. 23, 2009

Related U.S. Application Data

(60) Provisional application No. 61/022,172, filed on Jan. 18, 2008.

(51) Int. Cl.
| C07D 205/08 | (2006.01) |
| A61K 31/397 | (2006.01) |
| A61P 27/06 | (2006.01) |
| A61P 17/14 | (2006.01) |
| C07D 409/06 | (2006.01) |

(52) U.S. Cl. ............... 514/210.02; 540/200; 514/210.15
(58) Field of Classification Search .................. 540/200; 514/210.02, 210.15 C
See application file for complete search history.

(56) References Cited

U.S. PATENT DOCUMENTS

| 4,166,452 A | 9/1979 | Generales |
| 4,256,108 A | 3/1981 | Theeuwes |
| 4,265,874 A | 5/1981 | Bonsen |
| 5,462,968 A | 10/1995 | Woodward |
| 5,698,598 A | 12/1997 | Woodward |
| 6,090,847 A | 7/2000 | Woodward |
| 6,437,146 B1 | 8/2002 | Hattori |
| 6,710,072 B2 | 3/2004 | Burk |
| 6,747,054 B2 | 6/2004 | Cameron |
| 7,091,231 B2 | 8/2006 | Donde |
| 7,674,786 B2* | 3/2010 | Old et al. .................. 514/210.02 |
| 7,772,392 B2* | 8/2010 | Old et al. ...................... 540/200 |
| 2003/0120079 A1 | 6/2003 | Elworthy |
| 2003/0207925 A1 | 11/2003 | Cameron |
| 2009/0227557 A1* | 9/2009 | Old ........................... 514/210.02 |
| 2009/0318404 A1* | 12/2009 | Old ........................... 514/210.02 |

FOREIGN PATENT DOCUMENTS

WO    WO 94/13295    6/1994

OTHER PUBLICATIONS

Carey, Francis A.: Conformations of Alkanes and Cycloalkanes, Organic Chemistry, New York: McGraw-Hill Book Company 1987, p. 63.
Forro, E.; Fulop, F.: Synthesis of 4-aryl-substituted β-Lactam Enantionmers by Enzyme-Catalysed Kinetic Resolution. Tetrahedron: Asymmetry 12 (2001) 2351-2358.
Remington's Pharmaceutical Sciences, Mack Publishing Company, Easton, Pa., 16th Edition, 1980.

* cited by examiner

Primary Examiner — Mark Berch
(74) Attorney, Agent, or Firm — Kevin J. Forrestal; John E. Wurst; Allergan, Inc.

(57) ABSTRACT

Compounds comprising

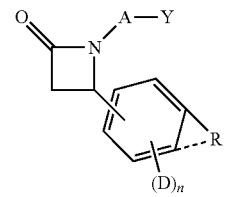

or a pharmaceutically acceptable salt or a prodrug thereof, are disclosed, wherein Y is

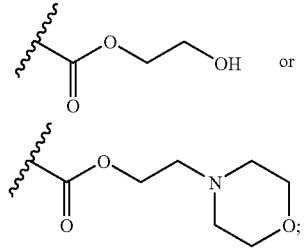

A is $—(CH_2)_6—$, cis $—CH_2CH=CH—(CH_2)_3—$, or $—CH_2C\equiv C—(CH_2)_3—$, wherein 1 or 2 carbon atoms may be substituted with S or O; or A is $—(CH_2)_m—Ar—(CH_2)_o—$ wherein Ar is substituted or unsubstituted phenyl or monocyclic heteroaryl, the sum of m and o is from 1 to 4, and wherein one $CH_2$ may be replaced with S or O; X is S or O; R is a hydrocarbyl or a hydroxyhydrocarbyl moiety having from 1 to 12 carbon atoms; D is independently a moiety comprising from 1 to 6 non-hydrogen atoms; and n is an integer from 0 to 4. Methods, compositions, and medicaments related thereto are also disclosed.

20 Claims, No Drawings

THERAPEUTIC BETA-LACTAMS

CROSS-REFERENCE TO RELATED APPLICATION

This application is based, and claims priority under 35 U.S.C. §120 to U.S. Provisional Patent Application No. 61/022,172 filed on Jan. 18, 2008, and which is incorporated herein by reference.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

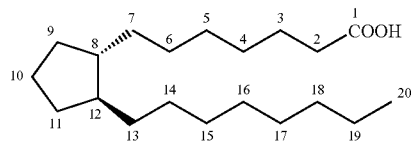

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

The prostaglandin E analog shown below is disclosed in the following documents, expressly incorporated herein by reference: U.S. Pat. No. 5,462,968; 5,698,598; and 6,090,847.

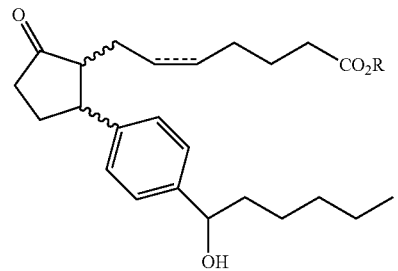

Other $EP_2$ selective agonists are disclosed in U.S. patent application Ser. No. 11/009,298, filed Dec. 10, 2004 (now U.S. Pat. No. 7,091,231 issued Aug. 15, 2006). Prostaglandin $EP_2$ selective agonists are believed to have several medical uses. For example, U.S. Pat. No. 6,437,146 teaches the use of prostaglandin $EP_2$ selective agonists "for treating or preventing inflammation and pain in joint and muscle (e.g., rheumatoid arthritis, rheumatoid spondylitis, osteoarthritis, gouty arthritis, juvenile arthritis, etc.), inflammatory skin condition (e.g., sunburn, burns, eczema, dermatitis, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Chrohn's disease, atrophic gastritis, gastritis varialoforme, ulcerative colitis, coeliac disease, regional ileitis, irritable bowel syndrome, etc.), gingivitis, inflammation, pain and tumescence after operation or injury, pyrexia, pain and other conditions associated with inflammation, allergic disease, systemic lupus crythematosus, scleroderma, polymyositis, tendinitis, bursitis, periarteritis nodose, rheumatic fever, Sjgren's syndrome, Behcet disease, thyroiditis, type I diabetes, diabetic complication (diabetic microangiopathy, diabetic retinopathy, diabetic neohropathy, etc.), nephrotic syndrome, aplastic anemia, myasthenia gravis, uveitis contact dermatitis, psoriasis, Kawasaki disease, sarcoidosis, Hodgkin's disease, Alzheimers disease, kidney dysfunction (nephritis, nephritic syndrome, etc.), liver dysfunction (hepatitis, cirrhosis, etc.), gastrointestinal dysfunction (diarrhea, inflammatory bowel disease, etc.) shock, bone disease characterized by abnormal bone metabolism such as osteoporosis (especially, postmenopausal osteoporosis), hypercalcemia, hyperparathyroidism, Paget's bone diseases, osteolysis, hypercalcemia of malignancy with or without bone metastases, rheumatoid arthritis, periodonritis, osteoarthritis, ostealgia, osteopenia, cancer cachexia, calculosis, lithiasis (especially, urolithiasis), solid carcinoma, mesangial proliferative glomerulonephritis, edema (e.g. cardiac edema, cerebral edema, etc.), hypertension such as malignant hypertension or the like, premenstrual tension, urinary calculus, oliguria such as the one caused by acute or chronic failure, hyperphosphaturia, or the like."

U.S. Pat. No 6,710,072 teaches the use of EP2 agonists for the treatment or prevention of "osteoporosis, constipation, renal disorders, sexual dysfunction, baldness, diabetes, cancer and in disorder of immune regulation . . . various pathophysiological diseases including acute myocardial infarction, vascular thrombosis, hypertension, pulmonary hypertension, ischemic heart disease, congestive heart failure, and angina pectoris."

SUMMARY OF THE INVENTION

Disclosed herein are compounds useful in treating glaucoma, inflammatory bowel disease, the stimulation of hair growth, and the stimulation of the conversion of vellus hair to terminal hair. The compounds themselves are disclosed below.

DESCRIPTION OF THE INVENTION

Disclosed herein are compounds comprising:

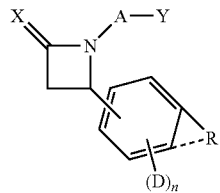

or a pharmaceutically acceptable salt or a prodrug thereof, wherein a dashed line represents the presence or absence of a covalent bond;

Y is

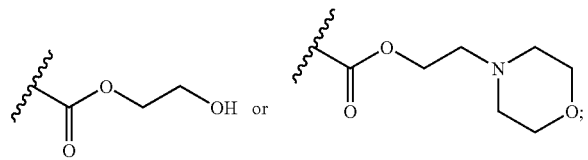

A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is substituted or unsubstituted phenyl or monocyclic heteroaryl, the sum of m and o is from 1 to 4, and wherein one $CH_2$ may be substituted with S or O;

X is S or O;

R is a hydrocarbyl or a hydroxyhydrocarbyl moiety comprising from 1 to 12 carbon atoms;

D is independently a moiety comprising from 1 to 6 non-hydrogen atoms; and n is an integer from 0 to 4.

Several of the carbon atoms on these compounds are chiral centers. While not intending to limit the scope of the invention in any way, or be bound in any way by theory, it is believed that many compounds and pharmaceutically active salts or prodrugs thereof having the stereochemistry shown below are particularly useful.

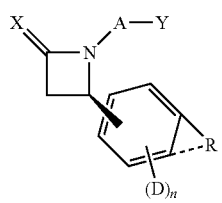

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, "represents a bond receding from the viewer."

In relation to the identity of A disclosed in the chemical structures presented herein, in the broadest sense, A is $-(CH_2)_6-$, cis $-CH_2CH=CH-(CH_2)_3-$, or $-CH_2C\equiv C-(CH_2)_3-$, wherein 1 or 2 carbon atoms may be substituted with S or O; or A is $-(CH_2)_m-Ar-(CH_2)_o-$ wherein Ar is substituted or unsubstituted phenyl or monocyclic heteroaryl, the sum of m and o is from 1 to 3, and wherein one $CH_2$ may be substituted with S or O.

In other words, while not intending to be limiting, A may be $-(CH_2)_6-$, cis $-CH_2CH=CH-(CH_2)_3-$, or $-CH_2C\equiv C-(CH_2)_3-$.

Alternatively, A may be a group which is related to one of these three moieties in that any carbon is substituted with S or O. For example, while not intending to limit the scope of the invention in any way, A may be an S substituted moiety such as one of the following or the like.

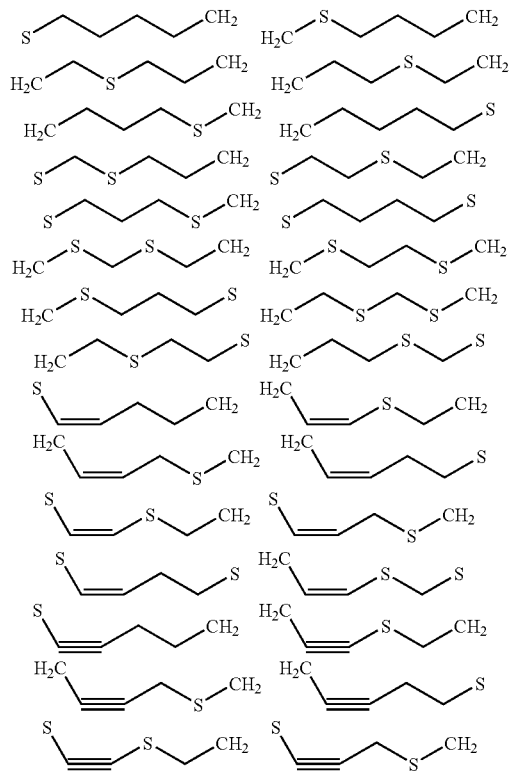

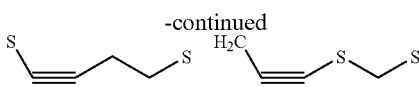

Alternatively, while not intending to limit the scope of the invention in any way, A may be an O substituted moiety such as one of the following or the like.

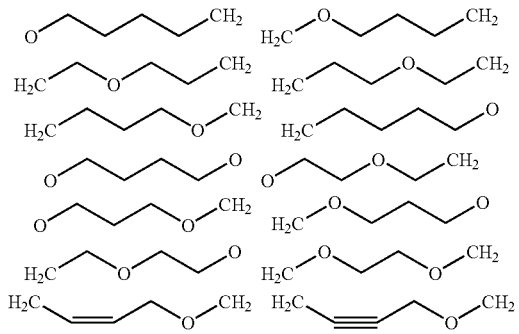

Alternatively, while not intending to limit the scope of the invention in any way, A may have both an O and an S substituted in the chain, such as one of the following or the like.

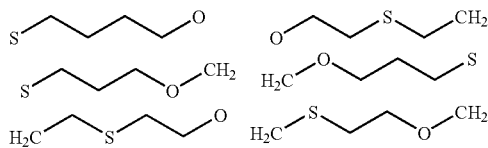

Alternatively, while not intending to limit the scope of the invention in any way, in certain embodiments A is —$(CH_2)_m$—Ar—$(CH_2)_o$— wherein Ar is substituted or unsubstituted phenyl or monocyclic heteroaryl, the sum of m and o is from 1 to 4, and wherein one $CH_2$ may be substituted with S or O. In other words, while not intending to limit the scope of the invention in any way, A comprises from 1 to 4 $CH_2$ moieties and Ar, e.g. —$CH_2$—Ar—, —$(CH_2)_2$—Ar—, —$CH_2$—Ar$CH_2$—, —$CH_2$Ar$(CH_2)_2$—, —$(CH_2)_2$—Ar $(CH_2)_2$—, and the like; or A comprises O, from 0 to 3 $CH_2$ moieties, and Ar, as in for example, —O—Ar—, Ar—$CH_2$—O—, —O—Ar—$(CH_2)_2$—, —O—$CH_2$—Ar—, —O—$CH_2$—Ar—$(CH_2)_2$, and the like; or A comprises S, from 0 to 3 $CH_2$ moieties, and Ar, as in for example, —S—Ar—, Ar—$CH_2$—S—, —S—Ar—$(CH_2)_2$—, —S—$CH_2$—Ar—, —S—$CH_2$—Ar—$(CH_2)_2$, and the like.

Ar is substituted or unsubstituted phenyl or substituted or unsubstituted monocyclic heteroaryl. In one embodiment, Ar is substituted or unsubstituted phenyl, thienyl, furyl, or pyridinyl. In another embodiment Ar is phenyl (Ph). In another embodiment A is —$(CH_2)_2$-Ph. While not intending to limit scope of the invention in any way, substituents may have 4 or less heavy atoms, or in other words, non hydrogen atoms. Any number of hydrogen atoms required for a particular substituent will also be included. Thus, the substituent may be $C_4$ or lower hydrocarbyl, including $C_4$ or lower alkyl, including methyl, ethyl, propyl isomers including isopropyl, butyl isomers including t-butyl, and alkenyl, alkynyl, and the like; $C_3$ or lower hydrocarbyloxy including alkoxy such as methoxy, ethoxy, etc.; $CF_3$; halo, such as F, Cl, or Br; hydroxyl; $NH_2$ and alkylamine functional groups up to $C_3$; other N or S containing substituents; and the like.

In one embodiment A is —$(CH_2)_m$—Ar—$(CH_2)_o$— wherein Ar is phenyl, the sum of m and o is from 1 to 3, and wherein one $CH_2$ may be substituted with S or O.

In another embodiment A is —$CH_2$—Ar—O$CH_2$—. In another embodiment A is —$CH_2$—Ar—O$CH_2$— and Ar is phenyl. In another embodiment, Ar is attached at the 1 and 3 positions, such as when A has the structure shown below.

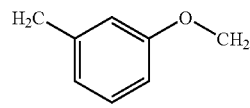

In another embodiment A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_2$-Ph- wherein one $CH_2$ may be substituted with S or O.

In another embodiment A is —$(CH_2)_6$—, cis —$CH_2CH$=$CH$—$(CH_2)_3$—, or —$CH_2C$≡$C$—$(CH_2)_3$—, wherein 1 or 2 carbon atoms may be substituted with S or O; or A is —$(CH_2)_2$-Ph-.

D is a moiety comprising from 1 to 6 non-hydrogen atoms, in other words, there are from 1 to 6 atoms which are not hydrogen, and any number of hydrogen atoms required to form the complete substituent. For example, a methyl substituent has 1 carbon atom and 3 hydrogen atoms. Other example substituents include other hydrocarbyl moieties comprising from 1 to 6 carbon atoms including alkyl such as ethyl, propyl, isopropyl, butyl and isomers thereof, pentyl and isomers thereof, hexyl and isomers thereof; cyclic and unsaturated hydrocarbyls having 1 to 6 carbon atoms; $CO_2H$ and salts thereof; alkoxy up to $C_5$ such as methoxy, ethoxy, propoxy, isopropoxy, a butoxy isomer, or a pentoxy isomer; carboxylic acid esters; CN; $NO_2$; $CF_3$; F; Cl; Br; I; sulfonyl esters; $SO_3H$ and salts thereof; and the like. D may be in any reasonable position on the phenyl ring.

In certain compounds, n is 0. In other compounds n is 1, in other compounds n is 2, and in other compounds n is 3.

A hydrocarbyl moiety refers to a moiety consisting of only carbon and hydrogen. While not intending to limit the scope of the invention in any way, examples of different types of hydrocarbyl moiety are as follows.

Hydrocarbyl is a moiety consisting of only carbon and hydrogen, and includes, but is not limited to alkyl, alkenyl, alkynyl, and the like, and in some cases aryl, and combinations thereof.

Alkyl is hydrocarbyl having no double or triple bonds including:

linear alkyl such as methyl, ethyl, propyl, n-butyl, n-pentyl, n-hexyl, and the like;

branched alkyl such as isopropyl, branched butyl isomers (i.e. sec-butyl, tert-butyl, etc), branched pentyl isomers (i.e. isopentyl, etc), branched hexyl isomers, and higher branched alkyl fragments;

cycloalkyl such as cyclopropyl, cyclobutyl, cyclopentyl, cyclohexyl, cycloheptyl, etc.; and alkyl fragments consisting of both cyclic and noncyclic components, whether linear or branched, which may be attached to the remainder of the molecule at any available position including terminal, internal, or ring carbon atoms.

Alkenyl is hydrocarbyl having one or more double bonds including linear alkenyl, branched alkenyl, cyclic alkenyl, and combinations thereof in analogy to alkyl.

Alkynyl is hydrocarbyl having one or more triple bonds including linear alkynyl, branched alkynyl, cyclic alkynyl and combinations thereof in analogy to alkyl.

Aryl is an unsubstituted or substituted aromatic ring or ring system such as phenyl, naphthyl, biphenyl, and the like. Aryl may or may not be hydrocarbyl, depending upon whether it has substituents with heteroatoms.

Arylalkyl is alkyl which is substituted with aryl. In other words alkyl connects aryl to the remaining part of the molecule. Examples are —CH$_2$-Phenyl, —CH$_2$—CH$_2$-Phenyl, and the like. Arylalkyl may or may not be hydrocarbyl, depending upon whether it has substituents with heteroatoms.

Another type of hydrocarbyl is alk(poly)enyl, which is similar to alkenyl, except that more than one double bond is present.

Another type of hydrocarbyl is alkynyl or an alk(poly)ynyl, which is similar to alkenyl or alk(poly)ynyl except that one or more triple bonds are present.

A hydrocarbyl moiety comprising a cyclic structure comprises a cycloalkyl, cycloalkenyl, cycloalkynyl, cycloalkyl(poly)enyl, cycloalkyl(poly)ynyl, aryl, and the like; and may consist of only the ring or may be a combination of the ring and one or more of the linear, branched, or cyclic hydrocarbyl fragments; or may be a fused polycyclic structure. Combinations of the above are also possible.

Additionally, combinations of any of the above in any manner imaginable to those of ordinary skill in the art are also hydrocarbyl.

For the compounds disclosed herein, hydrocarbyl having no ring has 12 or fewer carbon atoms, and hydrocarbyl having one or more rings has 18 or fewer carbon atoms.

A hydroxyhydrocarbyl moiety consists of a combination of a hydrocarbyl moiety and a hydroxyl group. In other words, a hydrogen atom of the hydrocarbyl moiety is substituted with a hydroxyl group. The hydroxyhydrocarbyl moiety attaches to the remainder of the molecule at a carbon atom.

Thus, while not intending to limit the scope of the invention in any way, as R is a hydrocarbyl or a hydroxyhydrocarbyl moiety comprising from 1 to 12 atoms, embodiments having R as any of the hydrocarbyl or hydroxycarbyl moieties listed above are specifically contemplated herein. R may also be a different moiety which may be considered hydrocarbyl or hydroxyhydrocarbyl according to the description given herein.

In other embodiments, R is not methyl, ethyl.

In other embodiments R comprises from 4 to 12 carbon atoms.

In certain compounds, R is a hydroxyhydrocarbyl having the hydroxyl group attached to the carbon atom which is also attached to the remainder of the molecule. In other words the hydroxyl group and the remainder of the molecule are on geminal positions on the hydrocarbyl moiety. This type of hydroxyhydrocarbyl moiety is referred to as a 1-hydroxyhydrocarbyl moiety herein. Non-linear hydroxyhydrocarbyl is hydroxyhydrocarbyl wherein the hydrocarbyl portion is not linear, i.e. it has branching and/or a ring.

In other compounds R is hydroxyhydrocarbyl where there are two carbon atoms connecting the hydroxyl group to the remaining part of the molecule. These particular hydroxyhydrocarbyl are called 2-hydroxyhydrocarbyl herein. For example, —CH$_2$CH$_2$OH and —C(CH$_3$)$_2$CH$_2$OH are 2-hydroxyhydrocarbyl. While not intending to limit the scope of the invention in any way, an example of a structure where R is 2-hydrocarbyl is shown below.

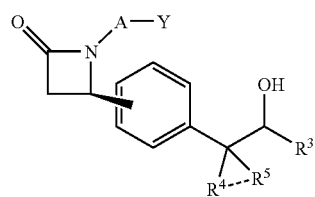

As with all other structures shown herein, pharmaceutically acceptable salts and prodrugs of compounds represent by these structures are also contemplated.

In one embodiment related to the above structure, R$^3$, R$^4$, and R$^5$ are independently H or C$_{1-6}$ alkyl. As the dashed line indicates the presence or absence of a bond, R$^4$ and R$^5$ may be two separate moieties. For example, while not intending to be limiting, R$^4$ and R$^5$ may be methyl, and no bond would be present where indicated by the dashed line. Alternatively, while not intending to limit the scope of the invention in any way, R$^4$ and R$^5$ may form a ring. In other words, a compound such as the one shown below is possible, wherein x is from 1 to 6.

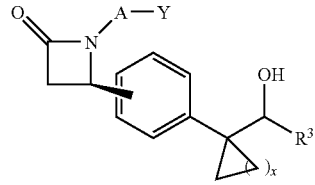

Pharmaceutically acceptable salts and prodrugs of compounds represent by these structures are also contemplated.

In certain compounds, R comprises from 6 to 9 carbon atoms and a cyclic structure. In other compounds, R comprises from 1 to 5 carbon atoms. In certain compounds R is hydroxyalkyl having from 1 to 5 carbon atoms. In other compounds R is a 1-hydroxyhydrocarbyl moiety comprising from 6 to 9 carbon atoms and a cyclic structure. In other compounds R is a 1-hydroxyhydrocarbyl moiety comprising from 6 to 9 carbon atoms and a cyclic structure comprising from 4-7 carbon atoms. In other words, the cyclic structure part of R is a cyclobutyl, cyclopentyl, cyclohexyl, or cycloheptyl fragment. The cyclic structure part of R may also be a cycloalkenyl or cycloalkynyl fragment such as cyclopentene or cyclohexene. In other compounds R is a hydrocarbyl moiety comprising from 1 to 5 carbon atoms. In other words, R is methyl, ethyl, propyl, isopropyl, a butyl isomer such as t-butyl, or a pentyl isomer. In certain compounds R is t-butyl.

Certain R groups are specifically contemplated herein. These are shown below, where PR represents the remaining part of the molecule.

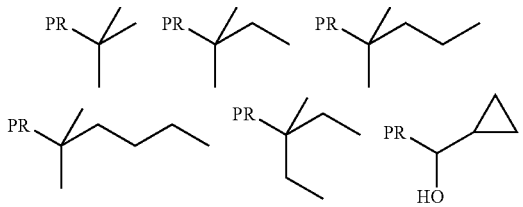

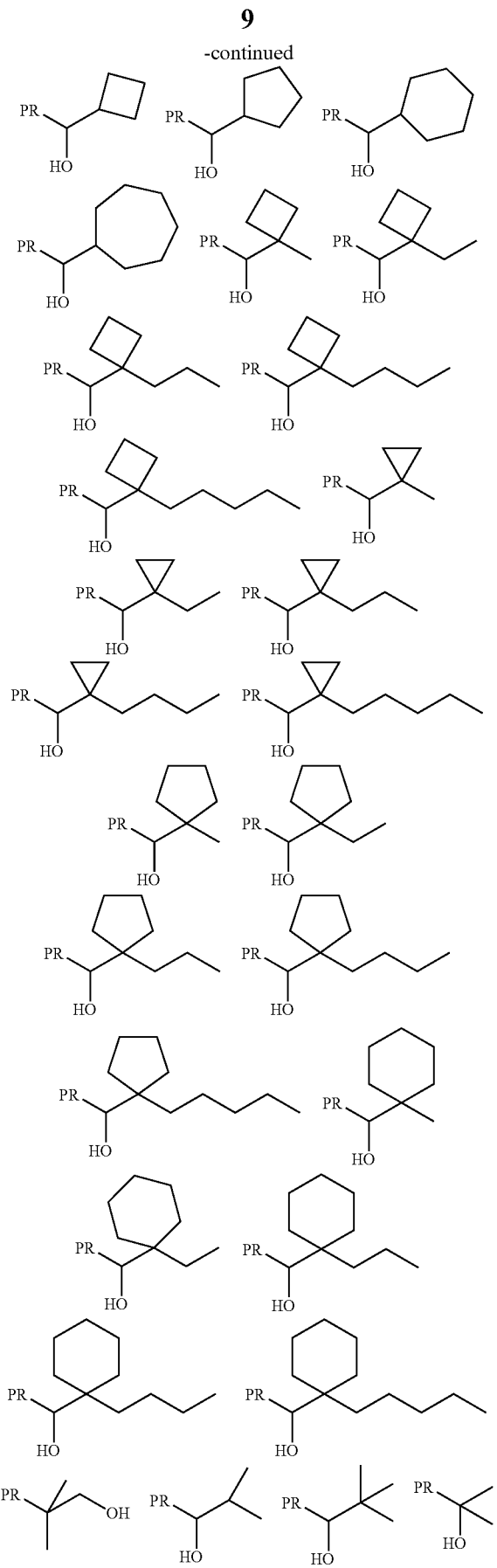

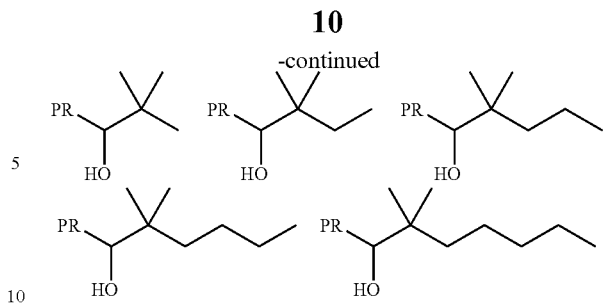

As there is a dashed line between R and the phenyl ring, cyclic structures having two carbon atoms of the phenyl ring are possible. While not intending to limit the scope of the invention in any way, compounds such as those represented by the structure below are therefore possible.

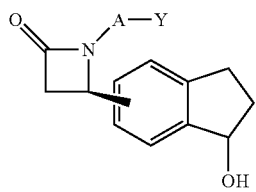

Pharmaceutically acceptable salts and prodrugs thereof are also contemplated.

Other useful compounds comprise

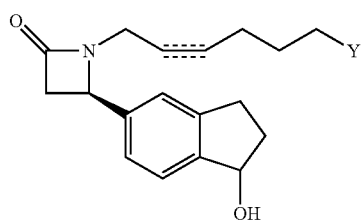

or a pharmaceutically acceptable salt, or a prodrug thereof.

Certain useful compounds comprise

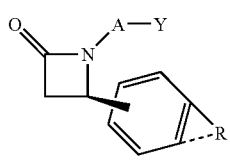

or a pharmaceutically acceptable salt, or a prodrug thereof.

Other useful examples of compounds comprise

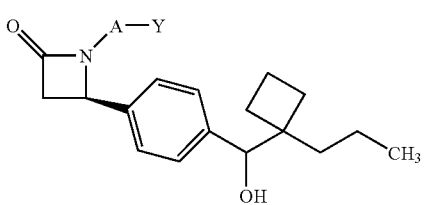

or a pharmaceutically acceptable salt, or a prodrug thereof.

Other compounds comprise

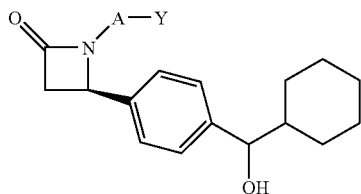

or a pharmaceutically acceptable salt, or a prodrug thereof.
Other embodiments comprise

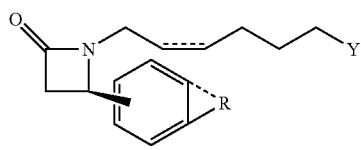

or a pharmaceutically acceptable salt, or a prodrug thereof, wherein a dashed line indicates the presence or absence of a bond.

Other compounds comprise

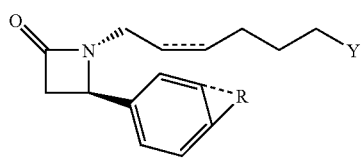

or a pharmaceutically acceptable salt or a prodrug thereof.
Other compounds comprise

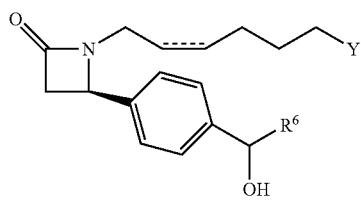

or a pharmaceutically acceptable salt, or a prodrug thereof, wherein $R^6$ is cycloalkyl comprising from 3 to 10 carbon atoms.

Other compounds comprise

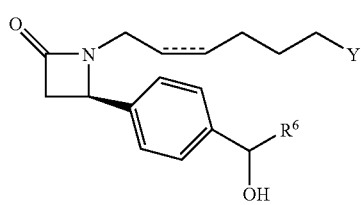

or a pharmaceutically acceptable salt, or a prodrug thereof, wherein $R^6$ is branched alkyl comprising from 3 to 10 carbon atoms.

Other compounds comprise

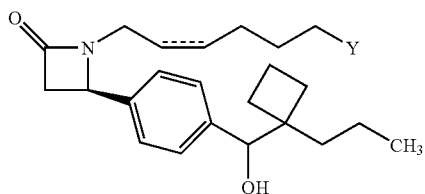

or a pharmaceutically acceptable salt, or a prodrug thereof.
Other embodiments comprise

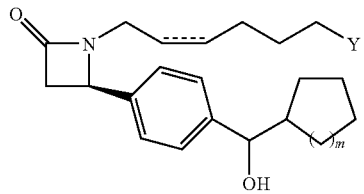

or a pharmaceutically acceptable salt, or a prodrug thereof wherein m is an integer having a value of from 0 to 3.

Those of ordinary skill in the art understand that any value which refers to the number of atoms, moieties, etc., on a small molecule will be an integer, i.e. 0, 1, 2, 3, etc.

Other compounds comprise

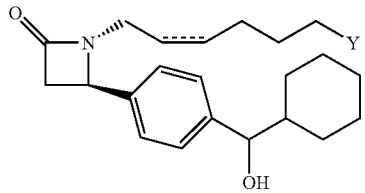

or a pharmaceutically acceptable salt, or a prodrug thereof.
Other compounds comprise

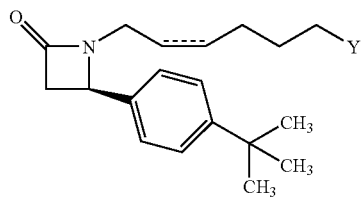

or a pharmaceutically acceptable salt, or a prodrug thereof.
Other useful compounds comprise

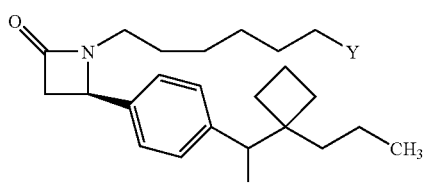

or a pharmaceutically acceptable salt, or a prodrug thereof.

13

Other compounds comprise

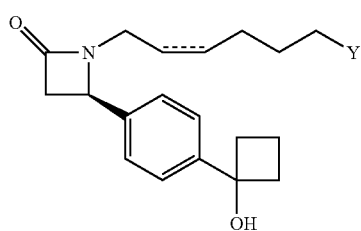

or a pharmaceutically acceptable salt or a prodrug thereof.

Other useful embodiments comprise

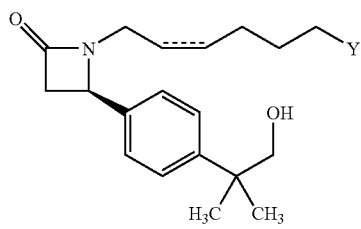

or a pharmaceutically acceptable salt or a prodrug thereof.

Other compounds comprise

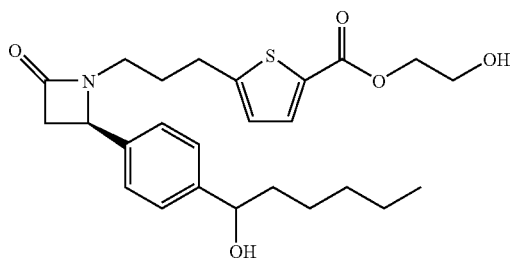

or a pharmaceutically acceptable salt or a prodrug thereof.

Other compounds comprise

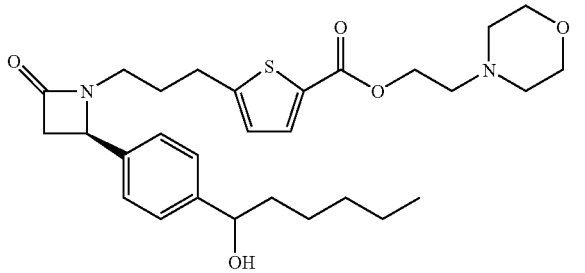

or a pharmaceutically acceptable salt or a prodrug thereof.

14

The following are examples of useful compounds

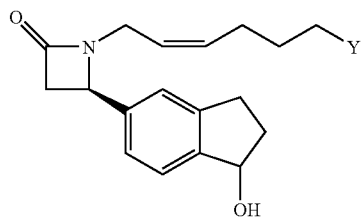

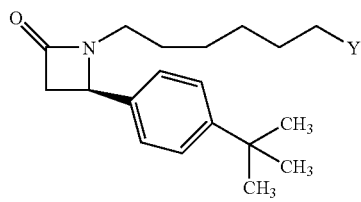

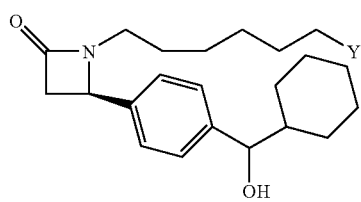

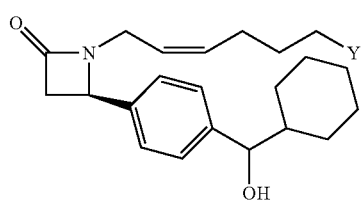

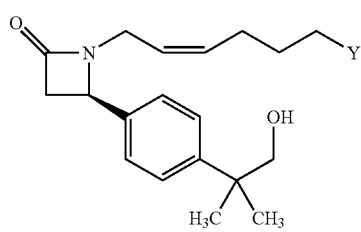

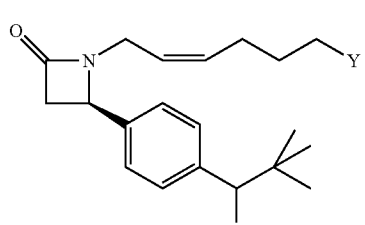

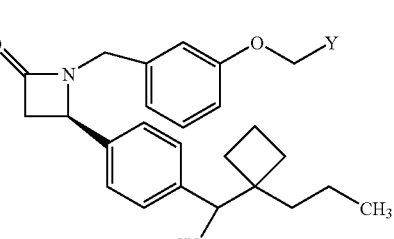

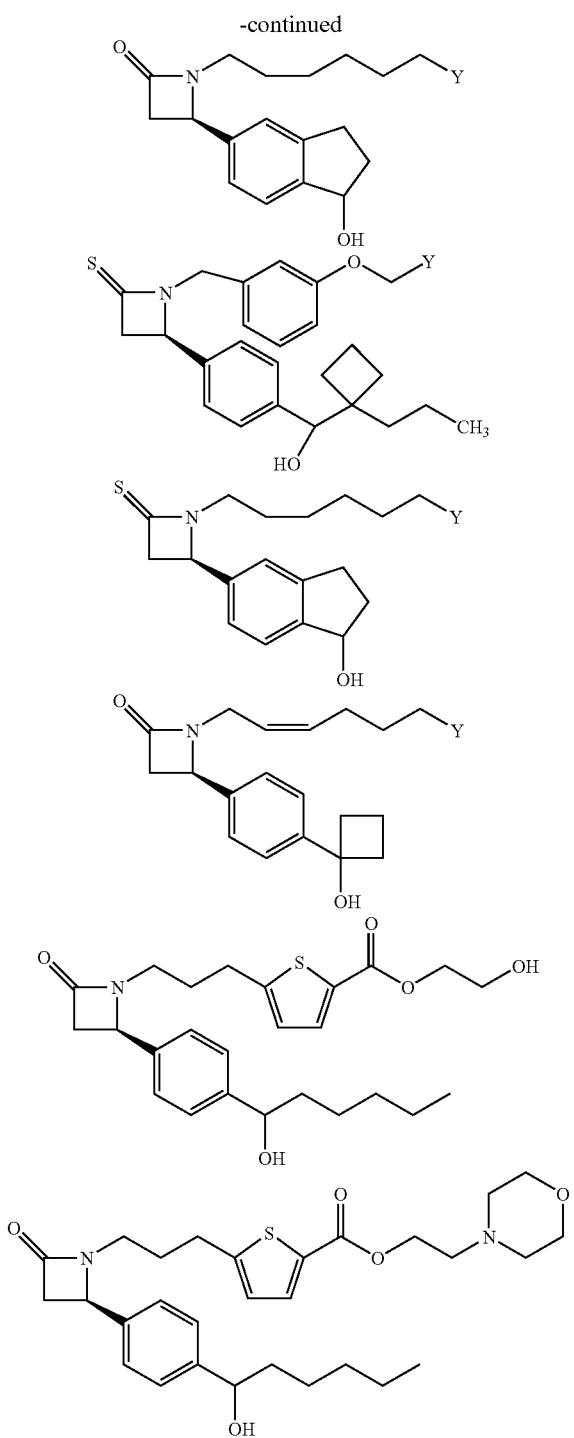

Pharmaceutically acceptable salts or prodrugs of these compounds are also useful.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into a salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

The compounds disclosed herein are useful for the prevention or treatment of glaucoma or ocular hypertension in mammals, or for the manufacture of a medicament for the treatment of glaucoma or ocular hypertension.

The compounds disclosed herein may also be useful for the stimulation of hair growth or stimulate conversion of vellus hair to terminal hair in mammals, or for the manufacture of a medicament for the stimulation of hair growth or stimulate conversion of vellus hair to terminal hair.

The compounds disclosed herein will be selective $EP_2$ agonists. Therefore, they are also useful for the treatment of those diseases disclosed in the art as being amenable to treatment by prostaglandin $EP_2$ agonist, such as the ones listed previously.

Ophthalmic Applications

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 or about 1 to about 100 mg/kg/day.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Applications for Stimulating Hair Growth

In one embodiment, the compounds disclosed herein can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so called bald person, although there is a noticeable absence of terminal hair, the skin does contain vellus hair, which is a fine colorless hair which may require microscopic examination to determine its presence. This vellus hair is a precursor to terminal hair.

The compounds described herein can be used to stimulate, such as the conversion of vellus hair to growth as terminal hair, as well as increasing the rate of growth of terminal hair. The utility of the compounds described herein for the simulation of hair growth was discovered as follows.

In the course of treating patients having glaucoma, treatment may only be appropriate in one eye. Within the course of daily practice, it was discovered that a patient who had been treated with bimatoprost, a prostaglandin analogue, developed lashed that were longer, thicker, and fuller in the treated eye than in the non-treated eye. On examination, the difference was found to be very striking. The lashes were longer and had a fuller, denser appearance in the treated eye. The lash appearance on the lids of the treated eyes would have appeared quite attractive if it represented a bilateral phenomenon. As a result of its asymmetric nature, the long lashes on one side could be construed as disturbing from a cosmetic standpoint. A systemic examination was preformed as a result of the asymmetric phenomenon. It soon became apparent that this altered appearance was not an isolated finding. Comparison of the lids of patients who were taking bimatoprost in only one eye revealed subtle changes in the lashed and adjacent hairs of the bimatoprost-treated side in several patients. Definite differences could be identified to varying degrees in the lashes and adjacent hairs of all patients who were taking the drug on a unilateral basis for longer than 6 months.

The changes in the lashes were apparent on gross inspection in several patients once attention was focused on the issue. In those with light colored hair and lashes, the differences were only seen easily with the aid of the high magnification and lighting capabilities of the slit lamp biomicroscope. In the course of glaucoma follow-up examination, attention is generally immediately focused on the eye itself. As a result of the high power magnification needed only one eye is seen at a time and the eye is seen at a high enough power that the lashes are not in focus. At these higher powers, any lash asymmetry between the two eyes is not likely to be noticed except by careful systematic comparison of the lashes and adjacent hairs of the eyelids of the two eyes.

Observed parameters leading to the conclusion that more robust hair growth occurred in the treatment area following administration of the prostaglandin analogue were multiple. They included increased length of lashed, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation of lashes and lash-like terminal hairs. The conclusion that hair growth is stimulated by prostaglandin analogues such as bimatoprost is thus supported not by evidence of a difference in a single parameter, but is based on multiple parameters of hair appearance in treated versus control areas in many subjects.

The compounds described herein are prostaglandin analogues and therefore have similar activities as bimatoprost, contain structural similarities, and therefore are expected to stimulate hair growth and stimulation of the conversion of vellus hair to terminal hair. In one embodiment, the compounds described herein and their prodrugs can be used for the stimulation of hair growth. As used herein, hair growth includes hair associated with the scalp, eyebrows, eyelids, beard, and other areas of the skin of animals.

In one embodiment, the compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more compounds as defined above and a dermatologically compatible carrier. Effective amounts of the active compounds may be determined by one of ordinary skill in the art, but will vary depending on the compound employed, frequency of application and desired result. The compound will generally range from about 0.0000001 to about 50% by weight of the dermatological composition. Preferably, the compound will range from about 0.001 to about 50% by weight of total dermatological composition, more preferably from about 0.1 to about 30% by weight of the composition.

In one embodiment, the application of the present compounds for stimulation of hair growth finds applications in mammalian species, including both humans and animals. In humans, the compounds described herein can be applied for example, to the scalp, face beard, head, pubic area, upper lip, eyebrows, and eyelids. In animal raised for their pelts, e.g., mink, the compounds described herein can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed herein relates to the use of a compound, as described herein, incorporated in a suitable pharmaceutical carrier, and applied at the site of thinning hair or baldness for exertion of local action. Accordingly, such topical compositions include those pharmaceutical forms in which the compound is applied externally by direct contact with the skin to be treated. Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, more preferably at least three months, and most preferably, at least six months.

For topical use on the eyelids or eyebrows, the active compounds can be formulated in aqueous solutions, creams, ointments, or oils exhibiting physologicla acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matricies may also be employed as well as soluble and insoluble ocular inserts, for instance, based on substances forming in situ gels. Depending on the actual formation and compound to be used, various amounts of the drug and different dose regimens may be employed. Typically, the daily amount of compound for treatment of the eyelid may be about 0.1 ng to about 100 mg per eyelid.

For topical use on the skin and scalp, the compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matricies for the slow release delivery may also be used. Typically, the dose to be applied on the scalp is in the range of about 0.1 ng to about 100 mg per day, more preferably about 1 ng to about 10 mg per day, and most preferably about 10 ng to about 1 mg per day depending on the compound and the formulation. To achieve the daily amount of medication depending on the formulation, the compound may be administered once or several times daily with or without antioxidants.

Specifically Contemplated Embodiments

In addition to any other embodiments disclosed herein, the following embodiments are specifically contemplated.

Compound Embodiment

A compound comprising

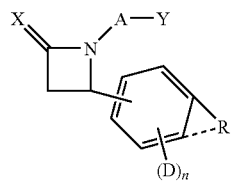

or a pharmaceutically acceptable salt or a prodrug thereof, wherein a dashed line represents the presence or absence of a covalent bond;

Y is

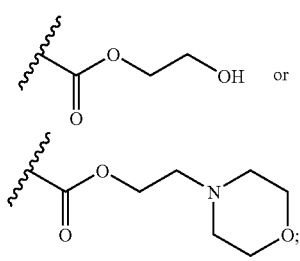

A is —(CH$_2$)$_6$—, cis —CH$_2$CH═CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is substituted or unsubstituted phenyl or monocyclic heteroaryl, the sum of m and o is from 1 to 4, and wherein one CH$_2$ may be substituted with S or O;

X is S or O;

R is a hydrocarbyl or a hydroxyhydrocarbyl moiety comprising from 1 to 12 carbon atoms;

D is independently a moiety comprising from 1 to 6 non-hydrogen atoms; and n is an integer from 0 to 4.

Another embodiment is a compound comprising

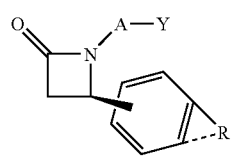

or a pharmaceutically acceptable salt, or a prodrug thereof; wherein Y, A, and R are as described above.

Another embodiment is a compound comprising

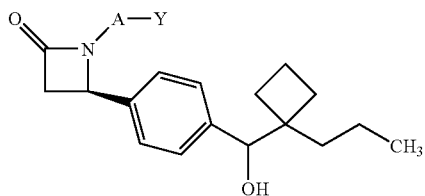

or a pharmaceutically acceptable salt, or a prodrug thereof;
Another embodiment is a compound comprising

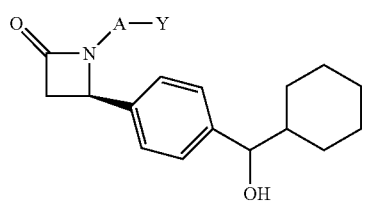

or a pharmaceutically acceptable salt, or a prodrug thereof; wherein A and Y are as described above.

Another embodiment is a compound comprising

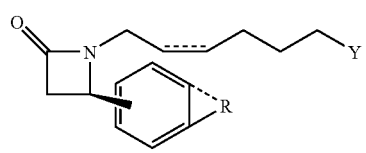

or a pharmaceutically acceptable salt, or a prodrug thereof; wherein Y and R are as described above.

Another embodiment is a compound comprising

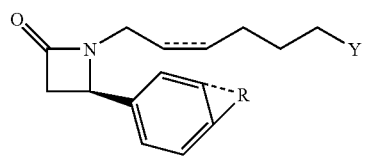

or a pharmaceutically acceptable salt, or a prodrug thereof; wherein Y is as described above; and R is alkyl having from 3 to 6 carbon atoms.

Another embodiment is a compound comprising

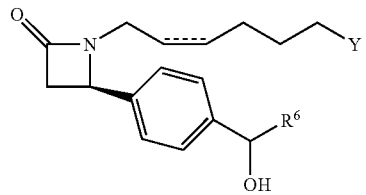

or a pharmaceutically acceptable salt, or a prodrug thereof, wherein Y is as described above; and R$^6$ is cycloalkyl comprising from 3 to 10 carbon atoms.

Another embodiment is a compound comprising

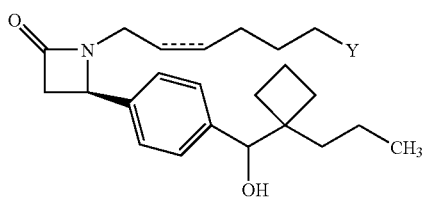

or a pharmaceutically acceptable salt, or a prodrug thereof; wherein Y is as described above.

Another embodiment is a compound comprising

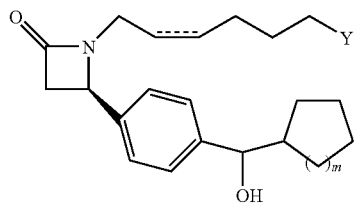

or a pharmaceutically acceptable salt, or a prodrug thereof; wherein Y is as described above; and m is an integer having a value of from 0 to 3.

Another embodiment is a compound comprising

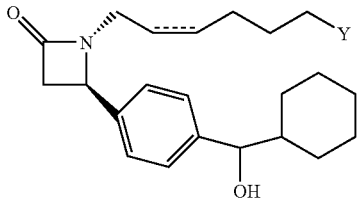

or a pharmaceutically acceptable salt, or a prodrug thereof; wherein Y is as described above.

Another embodiment is a compound comprising

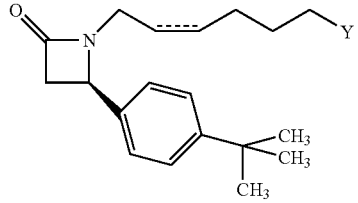

or a pharmaceutically acceptable salt, or a prodrug thereof, wherein Y is as described above.

Another embodiment is a compound comprising

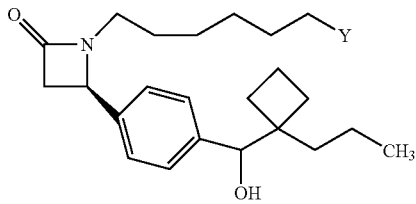

or a pharmaceutically acceptable salt, or a prodrug thereof. Another embodiment is a compound comprising

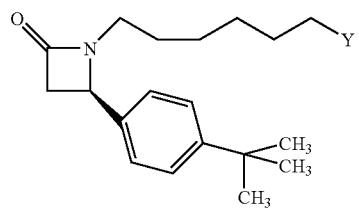

or a pharmaceutically acceptable salt, or a prodrug thereof, wherein Y is as described above.

Another embodiment is a compound comprising

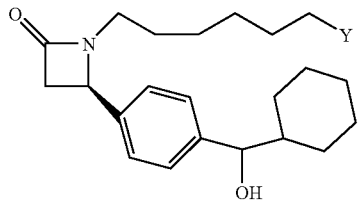

or a pharmaceutically acceptable salt, or a prodrug thereof, wherein Y is as described above.

Another embodiment is a compound comprising

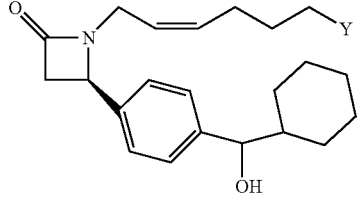

or a pharmaceutically acceptable salt, or a prodrug thereof, wherein Y is as described above.

Another embodiment is a compound comprising

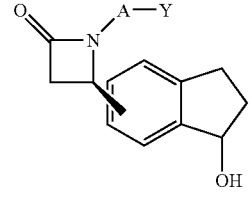

or a pharmaceutically acceptable salt or a prodrug thereof, wherein Y is as described above.

Another embodiment is a compound comprising

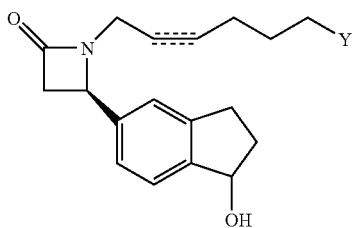

or a pharmaceutically acceptable salt or a prodrug thereof, wherein Y is as described above.

Another embodiment is a compound comprising

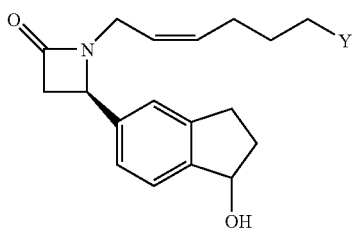

or a pharmaceutically acceptable salt or a prodrug thereof, wherein Y is as described above.

Another embodiment is a compound comprising

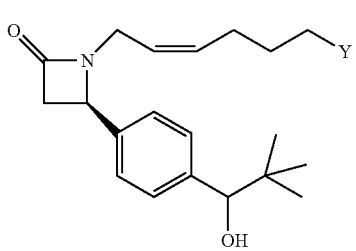

or a pharmaceutically acceptable salt or a prodrug thereof, wherein Y is as described above.

Another embodiment is a compound comprising

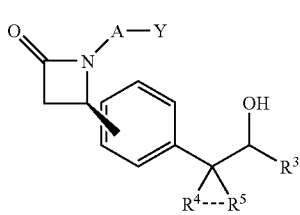

or a pharmaceutically acceptable salt or a prodrug thereof; wherein $R^3$, $R^4$, and $R^5$ are independently H or $C_{1-6}$ alkyl.

In another embodiment $R^4$ and $R^5$ are methyl in the structure above.

Another embodiment is a compound comprising

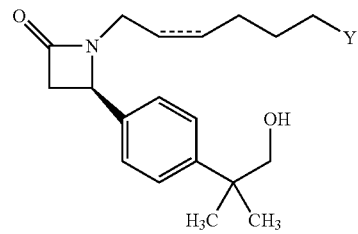

or a pharmaceutically acceptable salt or a prodrug thereof, wherein Y is as described above.

Another embodiment is a compound comprising

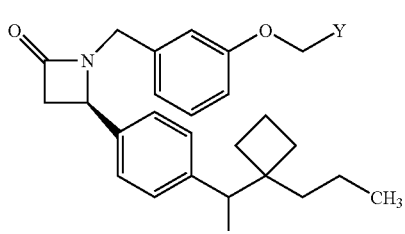

or a pharmaceutically acceptable salt or a prodrug thereof, wherein Y is as described above.

Another embodiment is a compound comprising

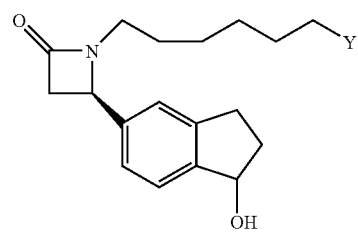

or a pharmaceutically acceptable salt or a prodrug thereof, wherein Y is as described above.

Another embodiment is a compound comprising

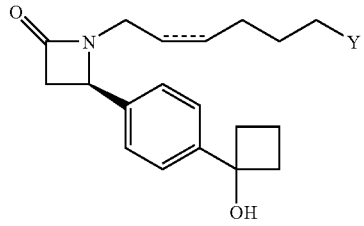

or a pharmaceutically acceptable salt or a prodrug thereof, wherein Y is as described above.

Another embodiment is a compound comprising

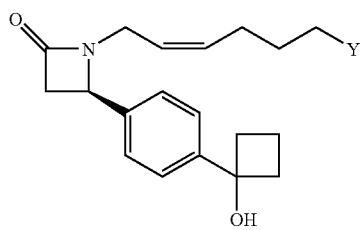

or a pharmaceutically acceptable salt or a prodrug thereof, wherein Y is as described above.

Another embodiment is a compound comprising

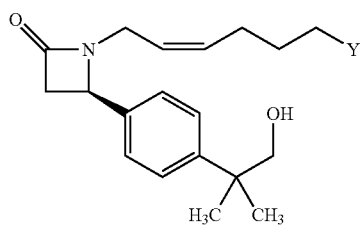

or a pharmaceutically acceptable salt or a prodrug thereof, wherein Y is as described above.

Other compounds comprise

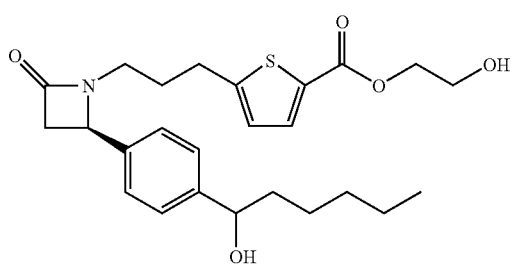

or a pharmaceutically acceptable salt or a prodrug thereof.

Other compounds comprise

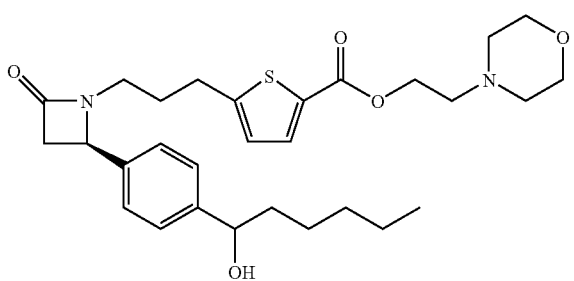

or a pharmaceutically acceptable salt or a prodrug thereof.

In another embodiment n is 0 in any structure shown above.

In another embodiment R comprises from 6 to 9 carbon atoms and a cyclic structure in any structure shown above.

In another embodiment R is a 1-hydroxyhydrocarbyl moiety in any structure shown above.

In another embodiment R comprises from 1 to 5 carbon atoms in any structure shown above.

In another embodiment R consists of t-butyl in any structure shown above.

In another embodiment R is 1-hydroxyalkyl in any structure shown above.

In another embodiment A is $-(CH_2)_6-$, cis $-CH_2CH=CH-(CH_2)_3-$, or $-CH_2C\equiv C-(CH_2)_3-$ in any structure shown above.

In another embodiment A is $-(CH_2)_m-Ar-(CH_2)_o-$ wherein Ar is phenyl, the sum of m and o is from 1 to 4, and wherein one $CH_2$ may be substituted with S or O in any structure shown above.

In another embodiment A is $-CH_2-Ar-O-CH_2-$ in any structure shown above.

In another embodiment R is 2-hydroxyhydrocarbyl in any structure shown above.

Method of Treating Embodiments

Glaucoma or Ocular Hypertension

For each embodiment drawn to a compound, a corresponding embodiment is contemplated drawn to administering the compound to a mammal for the treatment of glaucoma or ocular hypertension.

Inflammatory Bowel Disease

For each embodiment drawn to a compound, a corresponding embodiment is contemplated drawn to administering the compound to a mammal for the treatment of inflammatory bowel disease.

In another embodiment said inflammatory bowel disease is colitis.

In another embodiment said inflammatory bowel disease is Crohn's disease.

Baldness or Hair Loss

For each embodiment drawn to a compound, a corresponding embodiment is contemplated drawn to administering the compound to a mammal for the stimulation of hair growth or the stimulation of the conversion of vellus hair to terminal hair.

Method of Manufacturing Medicaments Embodiments

Glaucoma or Ocular Hypertension

For each embodiment drawn a compound, a corresponding embodiment is contemplated drawn to use of the compound in the manufacture of a medicament for the treatment of glaucoma.

Inflammatory Bowel Disease

One embodiment is a use of a compound in the manufacture of a medicament for the treatment of inflammatory bowel disease.

Baldness or Hair Loss

One embodiment is a use of a compound in the manufacture of a medicament for the stimulation of hair growth or the stimulation of the conversion of vellus hair to terminal hair.

In one embodiment, said compound can be used in the manufacture of a medicament for the treatment of glaucoma, treatment of inflammatory bowel disease, and/or stimulation of hair growth or the stimulation of the conversion of vellus hair to terminal hair, said compound comprising:

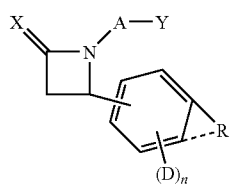

or a pharmaceutically acceptable salt or a prodrug thereof, wherein a dashed line represents the presence or absence of a covalent bond;

Y is

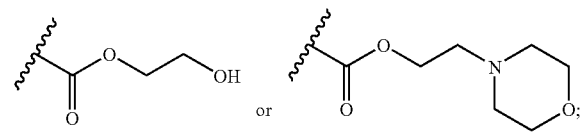

A is —(CH$_2$)$_6$—, cis —CH$_2$CH=CH—(CH$_2$)$_3$—, or —CH$_2$C≡C—(CH$_2$)$_3$—, wherein 1 or 2 carbon atoms may be substituted with S or O; or A is —(CH$_2$)$_m$—Ar—(CH$_2$)$_o$— wherein Ar is substituted or unsubstituted phenyl or monocyclic heteroaryl, the sum of m and o is from 1 to 4, and wherein one CH$_2$ may be substituted with S or O;

X is S or O;

R is a hydrocarbyl or a hydroxyhydrocarbyl moiety comprising from 1 to 12 carbon atoms;

D is independently a moiety comprising from 1 to 6 non-hydrogen atoms; and n is an integer from 0 to 4.

In another embodiment said compound comprises

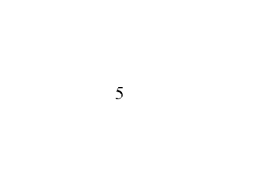

or a pharmaceutically acceptable salt, or a prodrug thereof; wherein Y, A, and R are as described above.

In another embodiment said compound comprises

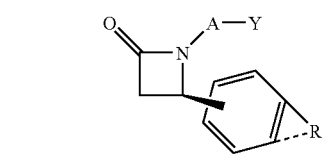

or a pharmaceutically acceptable salt, or a prodrug thereof.

In another embodiment said compound comprises

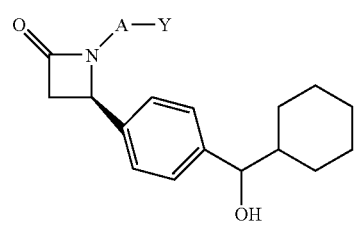

or a pharmaceutically acceptable salt, or a prodrug thereof; wherein A and Y are as described above.

In another embodiment said compound comprises

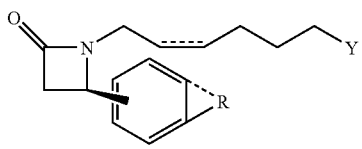

or a pharmaceutically acceptable salt, or a prodrug thereof; wherein Y and R are as described above.

In another embodiment said compound comprises

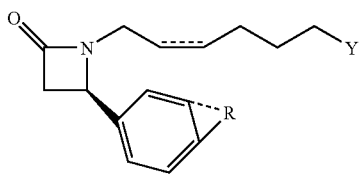

or a pharmaceutically acceptable salt, or a prodrug thereof; wherein Y is as described above; and R is alkyl having from 3 to 6 carbon atoms.

In another embodiment said compound comprises

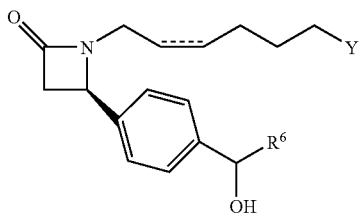

or a pharmaceutically acceptable salt, or a prodrug thereof, wherein Y is as described above; and R$^6$ is cycloalkyl comprising from 3 to 10 carbon atoms.

In another embodiment said compound comprises

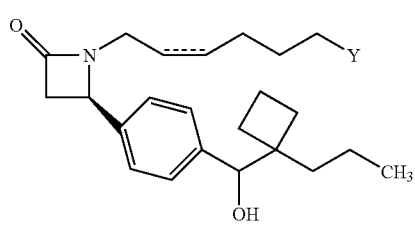

or a pharmaceutically acceptable salt, or a prodrug thereof; wherein Y is as described above.

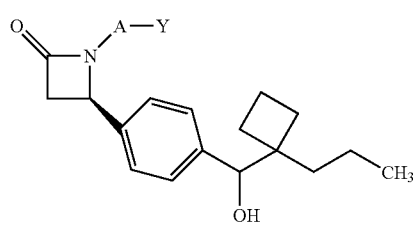

In another embodiment said compound comprises

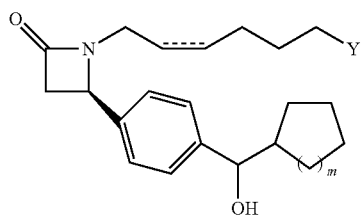

or a pharmaceutically acceptable salt, or a prodrug thereof; wherein Y is as described above; and m is an integer having a value of from 0 to 3.

In another embodiment said compound comprises

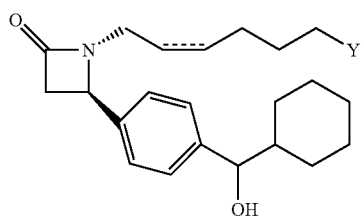

or a pharmaceutically acceptable salt, or a prodrug thereof; wherein Y is as described above.

In another embodiment said compound comprises

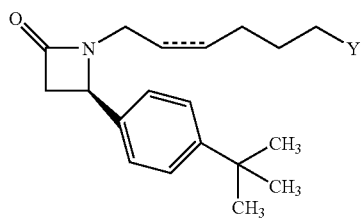

or a pharmaceutically acceptable salt, or a prodrug thereof, wherein Y is as described above.

In another embodiment said compound comprises

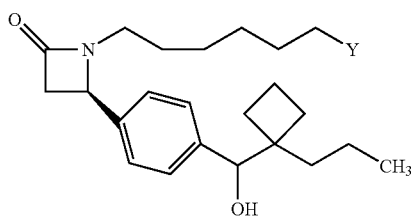

or a pharmaceutically acceptable salt, or a prodrug thereof.

In another embodiment said compound comprises

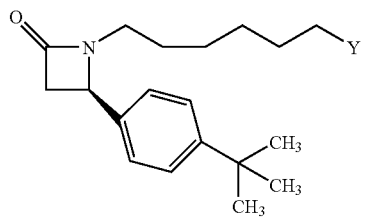

or a pharmaceutically acceptable salt, or a prodrug thereof, wherein Y is as described above.

In another embodiment said compound comprises

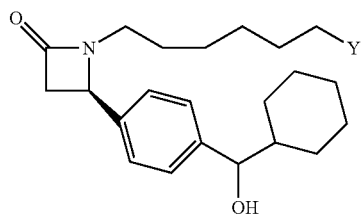

or a pharmaceutically acceptable salt, or a prodrug thereof, wherein Y is as described above.

In another embodiment said compound comprises

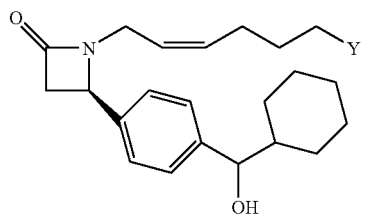

or a pharmaceutically acceptable salt, or a prodrug thereof, wherein Y is as described above.

In another embodiment said compound comprises

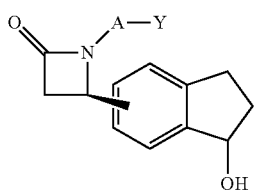

or a pharmaceutically acceptable salt or a prodrug thereof.

In another embodiment said compound comprises

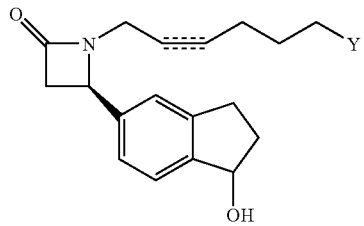

or a pharmaceutically acceptable salt or a prodrug thereof.

In another embodiment said compound comprises

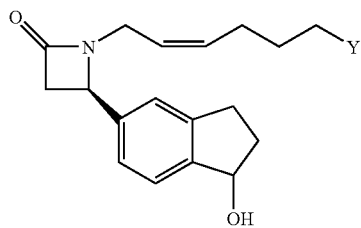

or a pharmaceutically acceptable salt or a prodrug thereof, wherein Y is as described above.

In another embodiment said compound comprises

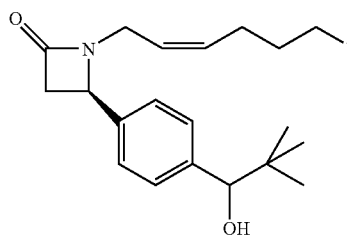

or a pharmaceutically acceptable salt or a prodrug thereof, wherein Y is as described above.

In another embodiment said compound comprises

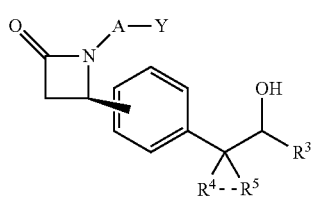

or a pharmaceutically acceptable salt or a prodrug thereof; wherein $R^3$, $R^4$, and $R^5$ are independently H or $C_{1-6}$ alkyl.

In another embodiment $R^4$ and $R^5$ are methyl in the structure above.

In another embodiment said compound comprises

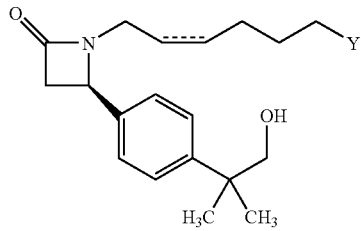

or a pharmaceutically acceptable salt or a prodrug thereof, wherein Y is as described above.

In another embodiment said compound comprises

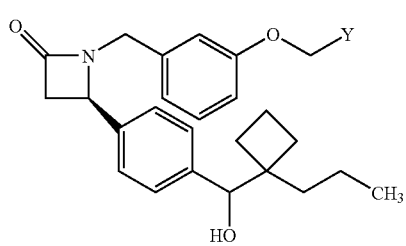

or a pharmaceutically acceptable salt or a prodrug thereof, wherein Y is as described above.

In another embodiment said compound comprises

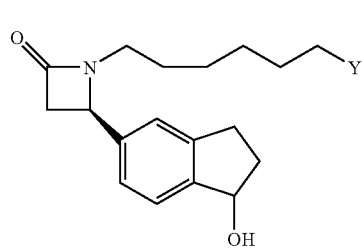

or a pharmaceutically acceptable salt or a prodrug thereof, wherein Y is as described above.

In another embodiment said compound comprises

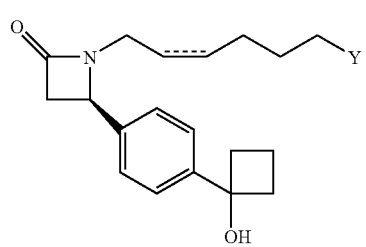

or a pharmaceutically acceptable salt or a prodrug thereof, wherein Y is as described above.

In another embodiment said compound comprises

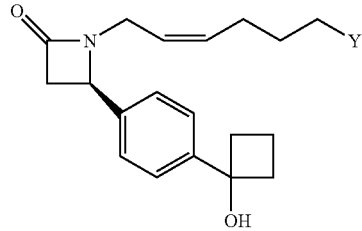

or a pharmaceutically acceptable salt or a prodrug thereof, wherein Y is as described above.

In another embodiment said compound comprises

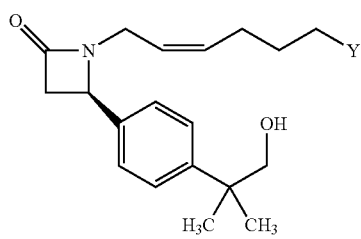

or a pharmaceutically acceptable salt or a prodrug thereof, wherein Y is as described above.

In another embodiment said compound comprises

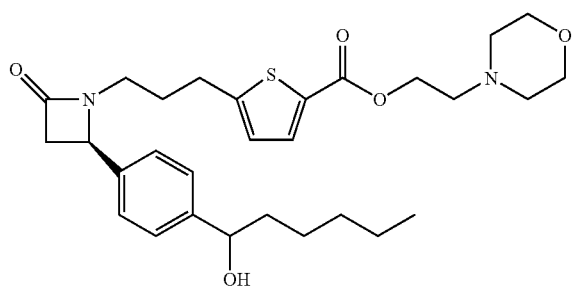

or a pharmaceutically acceptable salt or a prodrug thereof.

In another embodiment said compound comprises

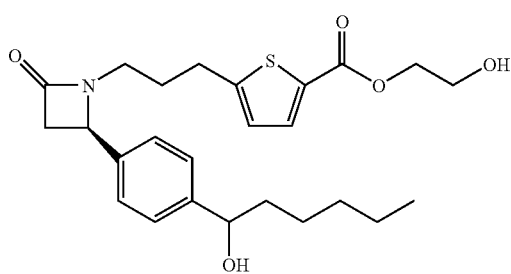

or a pharmaceutically acceptable salt or a prodrug thereof.

In another embodiment n is 0 in any structure shown above.

In another embodiment R comprises from 6 to 9 carbon atoms and a cyclic structure in any structure shown above.

In another embodiment R is a 1-hydroxyhydrocarbyl moiety in any structure shown above.

In another embodiment R comprises from 1 to 5 carbon atoms in any structure shown above.

In another embodiment R consists of t-butyl in any structure shown above.

In another embodiment R is 1-hydroxyalkyl in any structure shown above.

In another embodiment A is —(CH$_2$)$_6$—, cis —CH$_2$CH=CH—(CH$_2$)$_3$—, or —CH$_2$C≡C—(CH$_2$)$_3$— in any structure shown above.

In another embodiment A is —(CH$_2$)$_m$—Ar—(CH$_2$)$_o$— wherein Ar is phenyl, the sum of m and o is from 1 to 4, and wherein one CH$_2$ may be substituted with S or O in any structure shown above.

In another embodiment A is —CH$_2$—Ar—O—CH$_2$— in any structure shown above.

In another embodiment R is 2-hydroxyhydrocarbyl in any structure shown above.

In another embodiment said inflammatory bowel disease is colitis.

In another embodiment said inflammatory bowel disease is Crohn's disease.

Composition Embodiments

For each embodiment drawn to a compound, there is a corresponding embodiment drawn to a composition comprising said compound, wherein said composition is a liquid which is ophthalmically acceptable.

Synthetic Procedures

While there are many ways the compound disclosed herein may be prepared, in one method (Scheme 1) a vinyl benzaldehyde, commercially available from Aldrich, is treated with any appropriate alkyl metalate such as a lithiate, to form an alkylated alcohol. The resultant alcohols could then be protected and the resultant styrene derivatives could be treated as decribed by Forró and Fülöp (Tetrahedron: Assymmetry 12 (2001) 2351-2358) to form enantiomerically pure β-lactams. The α-chain may be then added by adapting procedures known in the art, such as those described in U.S. Patent Application Publication No. 20030207925, U.S. Patent Application Publication No. 20030120079, and U.S. Pat. No. 6,747,054.

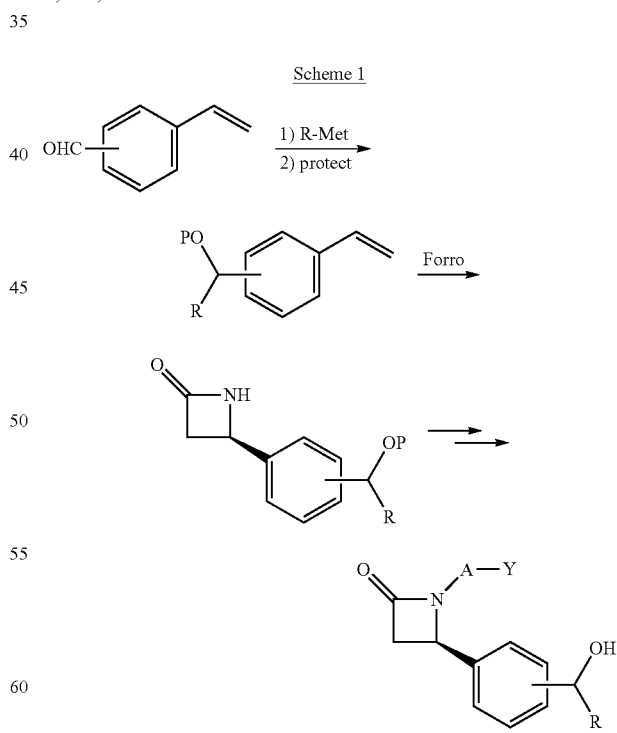

Alternatively (Scheme 2), a vinyl-substituted benzyl alcohol could be used as the substrate in the β-lactam forming reaction. Subsequent to β-lactam formation and introduction of the alpha chain (by the procedures discussed above), the benzylic alcohol is deprotected and oxidized to an aldehyde, which may be reacted by a nucleophile such as a Grignard reagent to complete the ω-chain and form the desired compound. See U.S. Pat. No. 7,091,231, filed Dec. 10, 2004, for an example of this method.

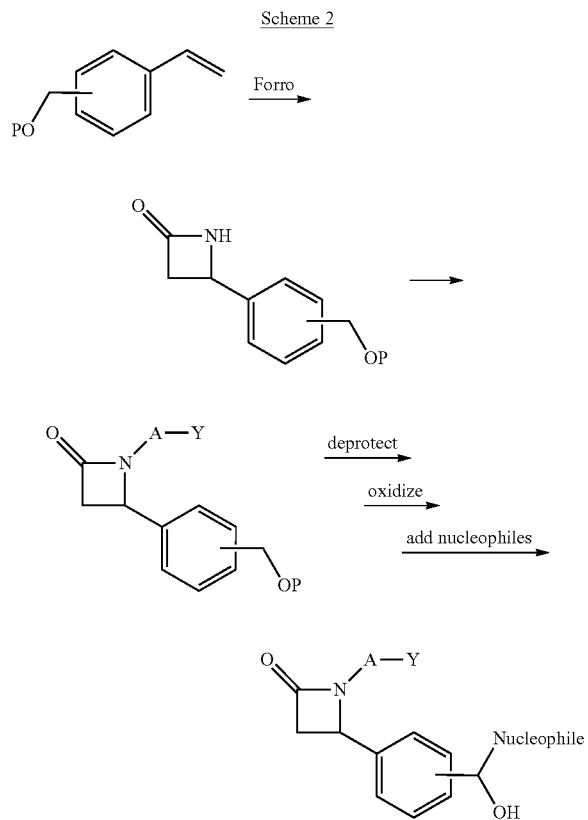

Another method of synthesis involves that of Scheme 3. Synthesis of Compound 1 below involves procedures outlined above. Introduction of the alpha chain (by the procedures discussed above) involves addition of methyl 5-(3-bromopropyl)thiophene-2-carboxylate (synthesis described in WO94/13295). The methyl ester is then converted to a carboxylic acid by ester hydrolysis, forming Compound 1.

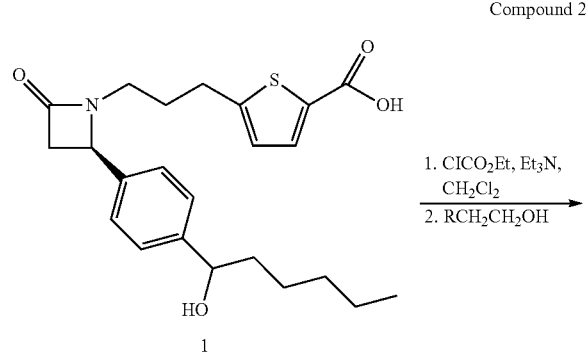

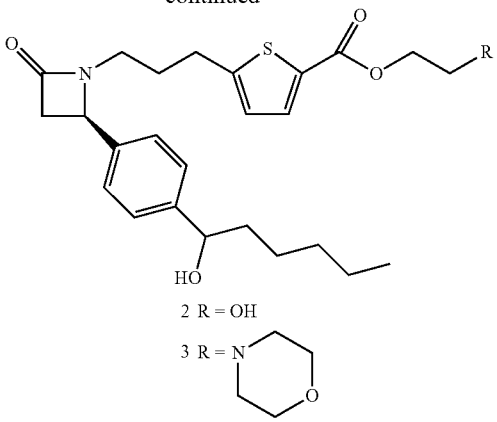

Triethylamine (15 μL) and ethyl chloroformate (15 μL) are added sequentially to a solution of compound 1 (10.5 mg) in $CH_2Cl_2$ (0.2 mL) at room temperature. After 2.5 h, triethylamine (15 μL) and ethylene glycol (200 μL) are added. After stirring overnight at room temperature, the reaction mixture is partitioned between $H_2O$ (5 mL) and $CH_2Cl_2$ (5 mL). The phases are separated and the aqueous phase is extracted with $CH_2Cl_2$ (2×5 mL). The combined organic phase is washed with 1 N HCl (5 mL) then dried ($MgSO_4$), filtered and concentrated in vacuo. Purification of the residue by flash column chromatography on silica gel (10% $CH_3OH/CH_2Cl_2$) affords 2.5 mg (22%) of the title compound 2.

Compound 3

Triethylamine (6.5 μL) and ethyl chloroformate (7 μL) are added sequentially to a solution of compound 1 (20 mg) in $CH_2Cl_2$ (0.47 mL) at room temperature. After 2.5 h, triethylamine (6.5 μL) and 4-(2-hydroxyethyl)-morphine (58 μL) are added. After stirring overnight at room temperature, the reaction mixture is partitioned between $H_2O$ (5 mL) and $CH_2Cl_2$ (5 mL). The phases are separated and the aqueous phase is extracted with $CH_2Cl_2$ (2×5 mL). The combined organic phase is washed with 1 N HCl (5 mL) then dried ($MgSO_4$), filtered and concentrated in vacuo. Purification of the residue by flash column chromatography on silica gel (10% $CH_3OH/CH_2Cl_2$) affords 5.1 mg (20%) of the title compound 3.

In Vivo Examples

Title compounds 2 and 3 from above are tested in vivo to measure its ability to reduce intraocular pressure. Compound 2 is tested in normotensive dogs. The intraocular pressure (IOP) decreases from baseline. This compound is also tested in laser-induced hypertensive monkeys, the IOP decreases from baseline.

Compound 3 is tested in normotensive dogs. The intraocular pressure (IOP) decreases from baseline. This compound is also tested in laser-induced hypertensive monkeys, the IOP decreases from baseline.

Biological Activity

The activity of compounds disclosed herein is tested according to the following procedures.

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors are washed with TME buffer, scraped from the bottom of the flasks, and homogenized for 30 sec using a Brinkman PT 10/35 polytron. TME buffer is added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate is centrifuged at 19000 r.p.m. for 20 min at 4° C. using a Beckman Ti-60 rotor. The resultant pellet is resuspended in TME buffer to give a final 1 mg/ml protein concentration, as determined by Biorad assay. Radioligand binding competition assays vs. [$^3$H—]17-phenyl $PGF_{2\alpha}$ (5 nM) are performed in a 100 µl volume for 60 min. Binding reactions are started by adding plasma membrane fraction. The reaction is terminated by the addition of 4 ml ice-cold TRIS-HCl buffer and rapid filtration through glass fiber GF/B filters using a Brandel cell harvester. The filters are washed 3 times with ice-cold buffer and oven dried for one hour. Non-specific binding is determined with 10 uM unlabeled 17-phenyl $PGF_{2\alpha}$.

[$^3$H—] $PGE_2$ (5 nM; specific activity 180 Ci mmol) is used as the radioligand for EP receptors. Binding studies employing $EP_1$, $EP_2$, $EP_3$, $EP_4$ are performed in duplicate in at least three separate experiments. A 200 µl assay volume is used. Incubations are for 60 min at 25° C. and are terminated by the addition of 4 ml of ice-cold 50 mM TRIS-HCl, followed by rapid filtration through Whatman GF/B filters and three additional 4 ml washes in a cell harvester (Brandel). Non-specific binding is determined with $10^{-5}$M of unlabeled $PGE_2$.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), are cultured in 100 mm culture dishes in high-glucose DMEM medium containing 10% fetal bovine serum, 2 mM I-glutamine, 250 µg/ml geneticin (G418) and 200 µg/ml hygromycin B as selection markers, and 100 units/ml penicillin G, 100 □g/ml streptomycin and 0.25 µg/ml amphotericin B.

(b) Calcium Signal Studies on the FLIPR™

Cells are seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells are then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 µM, plates are washed four times with HBSS-HEPES buffer to remove excess dye leaving 100 µL in each well. Plates are re-equilibrated to 37° C. for a few minutes.

Cells are excited with an Argon laser at 488 nm, and emission is measured through a 510-570 nm bandwidth emission filter (FLIPR™, Molecular Devices, Sunnyvale, Calif.). Drug solution is added in a 50 µl volume to each well to give the desired final concentration. The peak increase in fluorescence intensity is recorded for each well. On each plate, four wells each serve as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U-46619 (hTP), depending on receptor). The peak fluorescence change in each drug-containing well is then expressed relative to the controls.

Compounds are tested in a high-throughput (HTS) or concentration-response (CoRe) format. In the HTS format, forty-four compounds per plate are examined in duplicates at a concentration of $10^{-5}$ M. To generate concentration-response curves, four compounds per plate are tested in duplicates in a concentration range between $10^{-5}$ and $10^{-11}$ M. The duplicate values are averaged. In either, HTS or CoRe format each compound is tested on at least 3 separate plates using cells from different passages to give an $n \geq 3$.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound of the formula

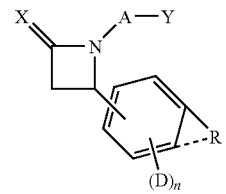

or a pharmaceutically acceptable salt or a prodrug thereof,
wherein a dashed line represents the presence or absence of a covalent bond;
Y is

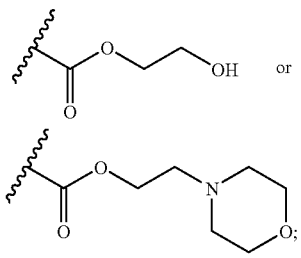

A is —$(CH_2)_6$—, cis —$CH_2CH$═$CH$—$(CH_2)_3$—, or —$CH_2C$≡$C$—$(CH_2)_3$—, wherein 1 or 2 carbon atoms may be substituted with S or O; or A is —$(CH_2)_m$—Ar—$(CH_2)_o$— wherein Ar is substituted or unsubstituted phenyl or monocyclic heteroaryl, the sum of m and o is from 1 to 4, and wherein one $CH_2$ may be replaced with S or O;

X is S or O;

R is a hydrocarbyl or a hydroxyhydrocarbyl moiety having from 1 to 12 carbon atoms;

D is independently a moiety comprising from 1 to 6 non-hydrogen atoms; and n is an integer from 0 to 4.

2. The compound of claim 1, wherein n is 0.

3. The compound of claim 1, wherein R comprises from 6 to 9 carbon atoms.

4. The compound of claim 3 of the formula

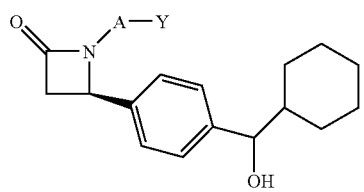

or a pharmaceutically acceptable salt, or a prodrug thereof.

5. The compound of claim 3 of the formula

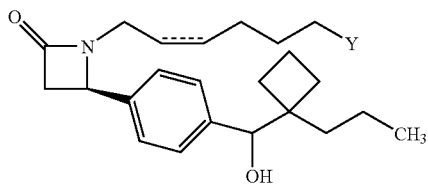

or a pharmaceutically acceptable salt, or a prodrug thereof.

6. The compound of claim 1 of the formula

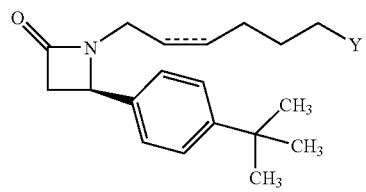

or a pharmaceutically acceptable salt, or a prodrug thereof.

7. The compound of claim 1 of the formula

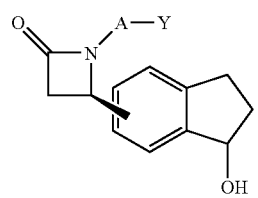

or a pharmaceutically acceptable salt or a prodrug thereof.

8. The compound of claim 1 wherein A is —$(CH_2)_6$—, cis —$CH_2CH=CH$—$(CH_2)_3$—, or —$CH_2C\equiv C$—$(CH_2)_3$—.

9. The compound of claim 2 of the formula

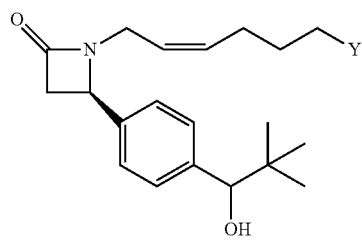

or a pharmaceutically acceptable salt or a prodrug thereof.

10. The compound of claim 2 of the formula

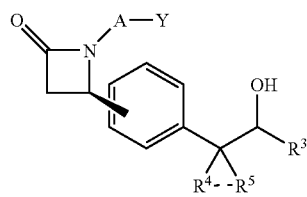

or a pharmaceutically acceptable salt or a prodrug thereof;

wherein $R^3$, $R^4$, and $R^5$ are independently H or $C_{1-6}$ alkyl and the dashed line indicates the presence or absence of a bond, $R^4$ and $R^5$ may be two separate moieties.

11. The compound of claim 10 wherein $R^4$ and $R^5$ are methyl.

12. The compound of claim 11 of the formula

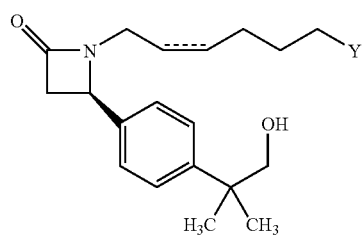

or a pharmaceutically acceptable salt or a prodrug thereof.

13. The compound of claim 2, wherein A is —$(CH_2)_m$—Ar—$(CH_2)_o$— wherein Ar is phenyl, the sum of m and o is from 1 to 4, and wherein one $CH_2$ may be replaced with S or O.

14. The compound of claim 1 of the formula

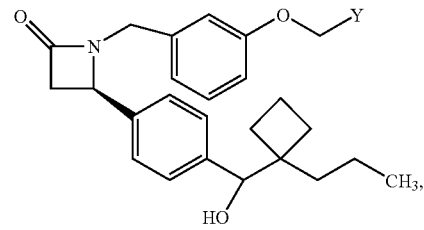

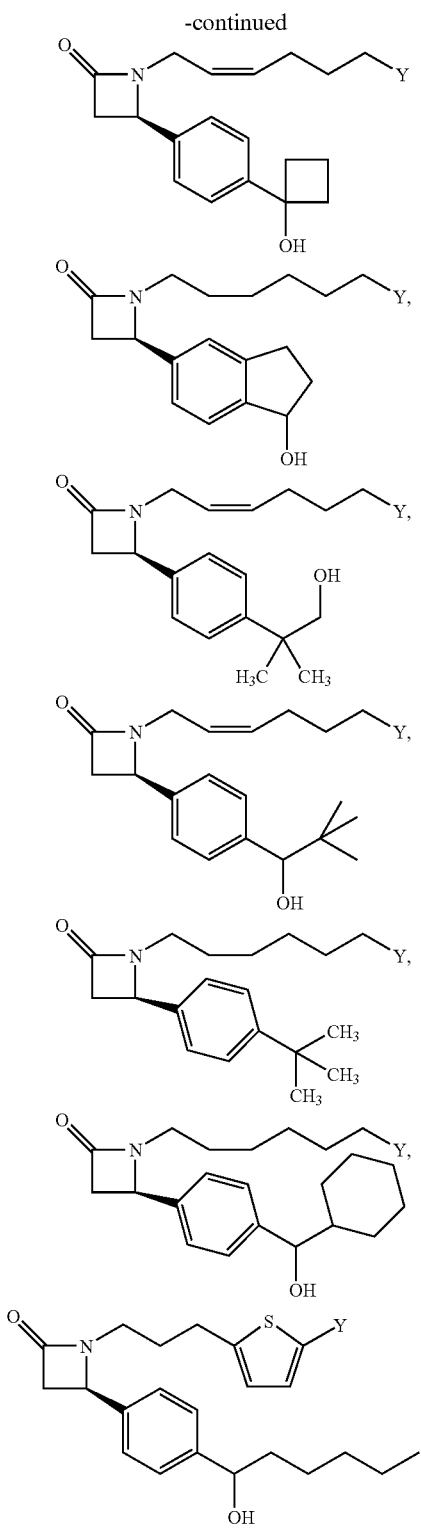

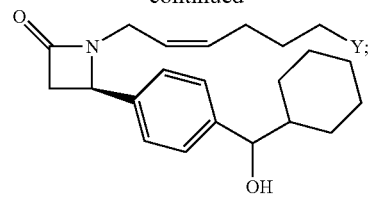

or a pharmaceutical acceptable salt or a prodrug thereof.

15. A method of treatment of glaucoma or ocular hypertension comprising administering a compound according to claim 1 to a mammal and treating glaucoma or ocular hypertension.

16. A composition comprising a compound according to claim 1, wherein said composition is a liquid which is ophthalmically acceptable and a pharmaceutically suitable carrier.

17. A method of treatment of baldness comprising administering a compound according to claim 1 to a mammal and treating baldness.

18. A method of treatment of hair loss comprising administering a compound according to claim 1 to a mammal and treating hair loss.

19. The compound of claim 1 of the formula:

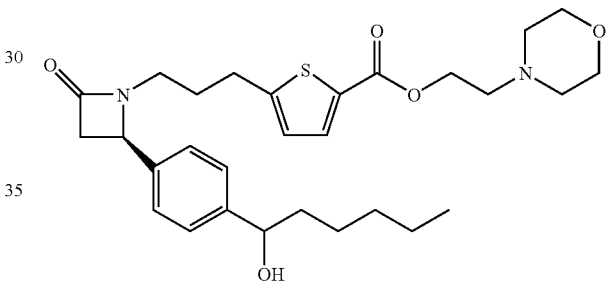

or a pharmaceutically acceptable salt or a prodrug thereof.

20. The compound of claim 1 of the formula:

or a pharmaceutically acceptable salt or a prodrug thereof.

* * * * *